United States Patent [19]

Grimmer et al.

[11] Patent Number: 5,300,303
[45] Date of Patent: Apr. 5, 1994

[54] SPRAY GRANULES OR MICROGRANULES OF PURE RIBOFLAVIN WHICH CONTAIN NO BINDER ARE NON-DUSTING AND FREE-FLOWING, AND THE PREPARATION THEREOF

[75] Inventors: Johannes Grimmer, Ludwigshafen; Hans Kiefer, Wachenheim; Christoph Martin, Mannheim, all of Fed. Rep. of Germany

[73] Assignee: BASF Aktiengesellschaft, Ludwigshafen, Fed. Rep. of Germany

[21] Appl. No.: 920,539

[22] Filed: Jul. 28, 1992

Related U.S. Application Data

[63] Continuation of Ser. No. 692,854, Apr. 29, 1991, abandoned.

[30] Foreign Application Priority Data

May 4, 1990 [DE] Fed. Rep. of Germany ....... 4014262

[51] Int. Cl.$^5$ ................ A61K 9/14; A61K 31/525
[52] U.S. Cl. ................................. 424/489; 426/471
[58] Field of Search ................ 424/489; 514/251; 426/471; 264/109, 114, 117

[56] References Cited

U.S. PATENT DOCUMENTS

| | | | |
|---|---|---|---|
| 4,710,519 | 12/1987 | Finnan et al. | 514/629 |
| 4,977,190 | 12/1990 | Meyer et al. | 514/951 |
| 4,994,458 | 2/1991 | Kilbride | 514/251 |
| 5,000,888 | 3/1991 | Killbride, Jr. et al. | 264/7 |

FOREIGN PATENT DOCUMENTS 0219276 4/1987 European Pat. Off. .

Primary Examiner—Thurman K. Page
Assistant Examiner—G. S. Kishore
Attorney, Agent, or Firm—Keil & Weinkauf

[57] ABSTRACT

A process for preparing spray granules or microgranules, which contain no binder, are non-dusting and free-flowing, from finely divided pure riboflavin, comprises subjecting an aqueous or water-containing suspension of the pure finely divided riboflavin to
 a) a fluidized bed spray drying
 b) a single-nozzle spray drying or
 c) a disk-type spray drying
in particular a fluidized bed spray drying, without adding binders to the suspension, and the spray granules or microgranules of riboflavin obtainable by this process.

10 Claims, No Drawings

SPRAY GRANULES OR MICROGRANULES OF PURE RIBOFLAVIN WHICH CONTAIN NO BINDER ARE NON-DUSTING AND FREE-FLOWING, AND THE PREPARATION THEREOF

This application is a continuation application of Ser. No. 07/692,854, filed Apr. 29, 1991, now abandoned.

The present invention relates to spray granules or microgranules of pure riboflavin which contain no binder, are non-dusting and free-flowing, and to a process for the preparation thereof from finely divided pure riboflavin.

Riboflavin (vitamin B2) is used widely in the foodstuffs and drugs industries as an essential or else only coloring additive to food products and drugs. When prepared by synthesis or obtained biotechnologically it is partly in the form of very finely divided powders and partly in the form of long yellow needles. Both types of riboflavin have very poor handling and flow properties.

For example, the finely divided powder is prone to dusting, has a very low bulk density (usually below 0.2 g/ml), easily picks up an electrostatic charge, flows poorly and therefore can be further processed only with great difficulty. Another serious disadvantage of the finely divided powder is that it cannot be used to produce tablets with a riboflavin content exceeding 25% by weight (cf. V. Bühler, "Vademecum for Vitamin Formulations", Wissenschaftliche Verlagsgesellschaft, Stuttgart, pages 98 to 99).

The riboflavin in the form of needles obtainable by slow crystallization at elevated temperature also gives rise to problems, because it flows poorly and because of the formation of dust and acquisition of charge, in further processing such as, for example, in the vitaminization of flour or on tableting.

In order to solve these problems, riboflavin has been partially granulated with the addition of auxiliaries in order to obtain a product which has acceptable flow and compression properties. Thus, EP-A-02 19276 describes vitamin-containing granules which contain 90–99 % vitamin and a binder.

Although these granules are very suitable for further industrial processing, whether for direct tableting or for preparing other riboflavin-containing drug products or human or animal foods containing vitamin B2, it is often unsatisfactory that they are not composed of pure active substance. This applies particularly to drug products because the pharmacopeia specifies a riboflavin with a minimum content of 98%.

In order to obtain riboflavin containing no binder for the drugs industry, in the process of EP-A-0 307 767 riboflavin is dissolved in a solvent and precipitated using a second solvent in which riboflavin is insoluble but which is miscible with the first solvent to give spherulitic crystals with good handling properties. However, this process is difficult to carry out industrially and is costly because large amounts of solvent are used and the resulting solvent mixtures have to be reprocessed.

It is an object of the present invention to develop a process which can be used to prepare from finely divided pure riboflavin in an industrially straightforward manner riboflavin granules which contain no binder and have properties making them easy to use industrially, i.e. granules which, on the one hand, are low-dusting, flow well, have a maximum bulk density and minimum electrostatic charge but, on the other hand, can be very finely divided again in a straightforward manner during further processing.

We have found that this object is achieved by the fluidized bed spray drying of an aqueous or water-containing suspension of finely divided pure riboflavin.

The present invention relates to a process for preparing spray granules or microgranules, which contain no binder, are non-dusting and free-flowing, from finely divided pure riboflavin, which comprises subjecting an aqueous or water-containing suspension of the pure finely divided riboflavin to
a) a fluidized bed spray drying
b) a single-fluid nozzle spray drying or
c) a disk-type spray drying without adding substantial amounts of binders to the suspension.

The process according to the invention is particularly advantageous when the aqueous or water-containing suspension of pure finely divided riboflavin is subjected to a fluidized bed spray drying.

The present invention also relates to spray granules or microgranules of pure riboflavin which contain no binder, are non-dusting and free-flowing, as are obtained by the process according to the invention.

The starting material used for the process according to the invention is finely divided pure riboflavin as obtained by prior art methods, for example by simply spray drying an aqueous suspension of riboflavin or else by rapid precipitation from acidified aqueous riboflavin solutions at below about 50° C., preferably 20° to 30° C., or else by rapid precipitation and rapid cooling of hot aqueous riboflavin solutions at a pH of from 0.8 to 6.5. This finely divided riboflavin normally has an average maximum particle diameter of about 0.1 to 50 $\mu$m, preferably 10 to 30 $\mu$m, and a bulk density of less than 0.2 g/ml.

Riboflavin in the form of larger needles, as is obtained,, for example, in the purification of crude riboflavin by the method of DE-A-3 421 714 by slow precipitation of riboflavin from acidic aqueous solutions at from 90° to 100° C., is not suitable in the form of its suspension as starting material for the process according to the invention. However, riboflavin in the form of larger needles which is obtained by slow precipitation at above 50° C. can be converted into suitable finely divided riboflavin by reprecipitation or by wet milling (e.g. in a colloid mill).

Pure riboflavin according to the invention is riboflavin with a purity of from 96 to 100, preferably 98 to 100, % and to which none of the conventional binders or granulating auxiliaries has been added.

The finely divided pure riboflavin is advantageously employed in the form of an aqueous suspension containing from 5 to 30, preferably 15 to 25, % by weight riboflavin. However, it is also possible to employ a suspension in a solvent which does not have too high a boiling point if this solvent contains water. The water content in the suspension should then be not less than about 10% by weight. Particularly suitable solvents are water-miscible solvents such as, for example, $C_1$-$C_4$-alkanols.

In contrast to the known spray drying of riboflavin solutions or suspensions, in which the latter are normally sprayed by means of a two-fluid nozzle into a drying tower, in the fluidized bed spray drying employed according to the invention the suspension is sprayed continuously or discontinuously into a fluidized bed of dry product. The drier is equipped with suitable apparatus to allow a defined particle size fraction to be obtained and the granulation process to be maintained (cf. K. Kröll, Trocknungstechnik, volume II "Trockner und Trocknungsverfahren", 2nd edition, Springer-Verlag, Berlin, 1978, pages 221 to 223). It is advantageous to use a spray drier having an integral fluidized bed (abbreviation: FSD=Fluidized Spray Drier) as described in Chem.-Ing.-Tech. 59 (1987) No. 2,pp. 112–117, especially page 115.

The fluidized bed spray drying, according to the invention, of riboflavin suspensions is generally carried out by a) introducing riboflavin in the form of a dry powder or of spray granules or microgranules into a fluidized bed drier in which the bed is kept at from 20° to 100° C., preferably 50° to 90° C., in particular 60° to 80° C., b) adding to this an aqueous or water-containing suspension of the finely divided riboflavin in sprayed form in accordance with the rate of drying, c) after a suitable residence time, drawing off the riboflavin particles from the fluidized bed and separating them into fractions in a suitable apparatus, d) ejecting the fraction with the particle size range from about 50 to 450 μm and e) returning the finer particles and/or the fine particles obtained by milling larger particles to the granulation process.

The fluidized bed spray drying can be carried out discontinuously or continuously. It is particularly advantageously carried out continuously.

To carry out the process it is initially necessary to prepare from dry riboflavin powder of the prior art a product which can be used to produce a fluidized bed. When the process is carried out discontinuously, a relatively finely divided product can be placed in the fluidized bed. The particle size range of the resulting dry product depends on the residence time of the particles in the drier. Particles in the size range from about 50 to 450 μm have the desired handling properties and are therefore the required product. Smaller particles, and riboflavin obtained by suitable milling of larger particles, are used as fluidized bed material for further batches.

To carry out the process continuously, the aqueous or water-containing suspension of finely divided riboflavin is continuously sprayed into a fluidized bed composed of dry riboflavin. The spraying rate is adjusted so that the fluidized bed has a temperature appropriate for the required degree of drying. It is accordingly determined in the final analysis by the difference between the entry and exit temperatures of the fluidizing gas.

In the continuous process, finely divided riboflavin is used in the fluidized bed only on first starting up the drier. The dry product obtained thereafter has a virtually constant particle size ratio. A defined portion of this is continuously removed and fractionated according to the particle size. The fraction in the particle size range from 50 to 450 μm is ejected as required product, and the fine particles and/or the fine particles obtained by milling larger particles are continuously returned to the fluidized bed to maintain the granulation process. In each case, the amount of riboflavin removed as required product is continuously sprayed into the fluidized bed in the form of the aqueous suspension of finely divided riboflavin.

The gas used to produce the fluidized bed generally enters at from 60 to 250, preferably 140° to 185° C. and exits at from 40 to 140, preferably 60° to 85° C., which results in the fluidized bed being at about 20 to 100, preferably 50° to 90° C., in particular 60° to 80° C.

The fluidized bed drying according to the invention generally results in the following particle size fractions, according to the conditions:

1. about 6 to 30% in the size range up to 100 μm 2. about 25 to 85% in the size range from 100 to 300 μm 3. about 1 to 70% in the size range from 250 to 400 μm.

The single-fluid nozzle spray drying according to the invention is generally carried out using a single-fluid hollow cone nozzle as marketed, for example, by Delawan under the name SDX-Standard. However, it is also possible to employ hollow cone nozzles supplied by Lechler, Schlick or Lurgi or those described in EP-A2 0 121 877. In this case, the energy of atomization is generated by the pressure of a pump which conveys the fluid to be dried to the single-fluid hollow-cone nozzle. The pressure required for atomization can be up to 80 bar absolute, but pressures of only from 15 to 25 bar absolute are preferably used. The solids content of the fluid to be dried can be up to 45% by weight, preferably 15 to 30% by weight.

The riboflavin suspension is introduced by means of the single-fluid hollow cone nozzle into a heated drying tower where it is dried and discharged at the lower end of the tower. The gas entering the drying tower is generally at from about 100 to 200, preferably 130° to 170° C., and the residence time is generally about 20 to 40 seconds. In order to obtain a non-dusting vitamin B2 microgranule fraction it is necessary for the dried product from the drying tower to be subjected to a suitable separation. The discharge cone of the drying tower can be designed to carry out this separation, as described in German patent 33 44 509, for example. This separation results in the non-dusting microgranules being deposited as required fractions, while the smaller particles (<20 μm) leave the drying tower with the gas. This fine material is removed from the gas in downstream separators (cyclones, filters) and can be mixed with the dry aqueous riboflavin suspensions (recycling). The proportion of the dusting fine fraction depends on the solids content of the suspension delivered to the hollow cone nozzle and on the admission pressure thereat. The proportion of fines may be from about 5 to 40%. The proportion of fines to be recycled is only about 5 to 10% when the solids content of the discharge is about 25 to 30% and the admission pressure of the nozzle is about 15 bar.

The product obtained in this way has particles in the size range from 30 to 200 μm.

The microgranules obtained in this way also have excellent handling properties.

It is also possible by disk-type spray drying of riboflavin suspensions, without addition of substantial amount of binders, to prepare microgranules which, after removal of the fines (<20 μm) as described above, have very good handling properties.

The spray granules or microgranules of riboflavin prepared in an industrially straight forward manner by the process according to the invention surprisingly have considerable advantages when used by comparison with commercial riboflavin products disclosed to date. They have particular advantages in applications where the presence of binders or granulation auxiliaries is unwanted.

EXAMPLE 1

About 2.5 kg/h of an approximately 20% strength aqueous suspension of a very finely divided riboflavin (bulk density about 0.1 kg/l; riboflavin content 99.5%; pharmaceutical product) at 20° C. were continuously sprayed through a two-fluid nozzle into a fluidized bed of riboflavin of approximately the same composition. The fluidizing gas entered at 170° C. The amount sprayed in was set so that the fluidized bed was at 71° to 72° C.

Portions of the fluidized bed were continuously removed and continuously separated into 3 particle fractions by screening. The resulting dry product had the following particle size distribution:

1) 20 to 30% in the size range <100 μm
2) 30 to 40% of the required product in the size range from 100 to 300 μm
3) 30 to 50% in the size range >300 μm.

The coarse fraction 3) was milled to particles in the size range <250 μm and then returned, together with the fine fraction 1), continuously to the fluidized bed.

About 0.5 kg/h of the required riboflavin spray granules (particle size range 125 to 250 μm) was obtained.

EXAMPLE 2

2.5 kg/h of an approximately 20% strength aqueous suspension of a very finely divided commercial riboflavin (bulk density about 0.1 kg/l; riboflavin content 96%; animal feed quality) were sprayed into a riboflavin fluidized bed. The fluidizing gas entered at 160° to 170° C. The amount sprayed in was set so that the fluidized bed was at 78° to 80° C.

About 0.5 kg/h of riboflavin spray granules with the required particle size range from 125 to 250 μm was obtained as in Example 1.

We claim:

1. A process for preparing spray granules having a particle size range from about 50 to 450 μm which contain no binder, are non-dusting and free-flowing, from finely divided riboflavin having a purity of 98 to 100%, an average maximum particle diameter of about 0.1 to 50 μm and a bulk density of less than 0.2 g/ml, which comprises: subjecting an aqueous binder-free suspension containing from 5 to 30% by weight of said finely divided riboflavin to fluidized bed spray drying at a temperature of from 20° to 100° C.

2. The process of claim 1, wherein the average maximum particle diameter of the finely divided riboflavin is from about 10 to 30 μm.

3. A process as defined in claim 1, wherein pure riboflavin obtained by rapid precipitation from acidified aqueous riboflavin solutions at below about 50° C. is used as said finely divided riboflavin.

4. A process as defined in claim 1, wherein pure riboflavin obtained by rapid precipitation and rapid cooling of hot aqueous riboflavin solutions at a pH of from 0.8 to 6.5 is used as said finely divided riboflavin.

5. A process as defined in claim 1, wherein pure riboflavin obtained in the purification of crude riboflavin by the method of by slow precipitation of riboflavin from acidic aqueous solutions at from 90° to 100° C. followed by reprecipitation as defined in claim 3 is used as said finely divided riboflavin.

6. A process as defined in claim 1, wherein pure riboflavin obtained in the purification of crude riboflavin by the method of by slow precipitation of riboflavin from acidic aqueous solutions at from 90° to 100° C. followed by reprecipitation as defined in claim 4 is used as said finely divided riboflavin.

7. A process as defined in claim 1, wherein pure riboflavin obtained in the purification of crude riboflavin by the method of by slow precipitation of riboflavin from acidic aqueous solutions at from 90° to 100° C. followed by wet milling in a colloid mill is used as said finely divided riboflavin.

8. The process of claim 1, wherein the fluidized bed spray drying is carried out by a) introducing pure, finely divided riboflavin having an average maximum particle diameter of about 0.1 to 50 μm in dry form into a fluidized bed drier in which the bed is kept at from 20° to 100° C.,
b) adding to this fluidized riboflavin bed the aqueous suspension of the pure finely divided riboflavin defined in claim 10 in sprayed form in accordance with the rate of drying,
c) maintaining the finely divided riboflavin defined in claim 10 in the fluidized bed until a substantial amount of the riboflavin has a particle size of from 50 to 450 μm, drawing off the riboflavin particles from the fluidized bed and separating them into fractions based on size,
d) ejecting the fraction with the particle size range from about 50 to 450 μm, and
e) returning the particles having a particle size finer than 50 μm and/or the fine particles obtained by milling the particles having a particle size larger than 450 μm to the granulation process.

9. The process of claim 8, wherein the fluidized bed spray drying is carried out continuously in a fluidized bed which is composed of spray granules or microgranules of pure riboflavin and is kept at from 50° to 90° C., and wherein a suitable portion of the resulting dry product is continuously removed from the fluidized bed and separated into particle fractions based on size.

10. The process of claim 9, wherein the fluidized bed of spray granules or microgranules is kept at from 60° to 80° C.

* * * * *

UNITED STATES PATENT AND TRADEMARK OFFICE
CERTIFICATE OF CORRECTION

PATENT NO. : 5,300,303
DATED : April 5, 1994
INVENTOR(S) : GRIMMER et al.

It is certified that error appears in the above-indentified patent and that said Letters Patent is hereby corrected as shown below:

Claim 5, column 6, lines 6-7, delete "by the method of".

Claim 6, column 6, lines 11-12, delete "by the method of".

Claim 7, column 6, lines 18-19, delete "by the method of".

Claim 8, column 6, line 31, "claim 10" should be -- claim 1--.

Claim 8, column 6, line 34, "claim 10" should be -- claim 1--.

Signed and Sealed this

Thirteenth Day of September, 1994

Attest:

BRUCE LEHMAN

Attesting Officer

Commissioner of Patents and Trademarks